United States Patent [19]

Norbury et al.

[11] Patent Number: 4,878,775
[45] Date of Patent: Nov. 7, 1989

[54] LIQUID TRANSFER DEVICE

[75] Inventors: R. James Norbury; Daniel B. Pendergrass, Jr., both of St. Paul, Minn.

[73] Assignee: Minnesota Mining and Manufacturing Company, St. Paul, Minn.

[21] Appl. No.: 114,435

[22] Filed: Oct. 28, 1987

[51] Int. Cl.$^4$ ..................... A61M 35/00; B05L 1/00
[52] U.S. Cl. .................... 401/132; 401/196; 604/306; 15/104.93
[58] Field of Search ............... 401/132, 196, 200, 261; 604/289, 306; 15/104.93; 128/114.1, 155, 156; 424/443, 447, 446

[56] References Cited

U.S. PATENT DOCUMENTS

| | | | |
|---|---|---|---|
| 2,579,403 | 12/1951 | Slomowitz et al. | 604/2 X |
| 3,196,478 | 7/1965 | Baymiller et al. | 401/132 |
| 3,334,374 | 8/1967 | Watkins, Jr. | 15/539 |
| 3,334,790 | 8/1967 | Eaton | 401/132 |
| 3,466,131 | 9/1969 | Arcudi | 401/132 |
| 3,472,675 | 10/1969 | Gordon et al. | 401/132 |
| 3,516,941 | 6/1970 | Matson | 252/316 |
| 3,619,842 | 11/1971 | Maierson | 401/132 X |
| 3,636,922 | 1/1972 | Ketner | 604/289 X |
| 3,640,629 | 2/1972 | Geiser | 401/132 |
| 3,768,916 | 10/1973 | Avery | 401/132 |
| 3,806,260 | 4/1974 | Miller | 401/132 X |
| 3,814,095 | 6/1974 | Lubens | 128/156 X |

FOREIGN PATENT DOCUMENTS 8100196 2/1981 Pct. Int'l. Appl. .................. 401/132

Primary Examiner—Richard J. Apley
Assistant Examiner—Franklin L. Gubernick
Attorney, Agent, or Firm—Donald M. Sell; Walter N. Kirn; Mark A. Litman

[57] ABSTRACT

A device provides liquid material for application to a surface. The device comprises in order at least a carrying substrate, frangible microcapsules containing the liquid to be applied, a raised area around the microcapsules of a structurally rigid material, and a flexible, liquid permeable material overlaying the microcapsules. Pressure on the liquid permeable material ruptures the microcapsules and enables the liquid to flow through the permeable material.

11 Claims, 1 Drawing Sheet

LIQUID TRANSFER DEVICE

BACKGROUND OF THE INVENTION

1. Field of the Invention

This invention relates to the application or transfer of relatively small amounts of liquid from a sampling device or applicator.

2. Background of the Art

It is often desirable to apply relatively imprecise amounts of liquid to a surface as when applying cosmetics, deodorants, medication or, cleansers to the body or applying cleansers, polishers, repellants, lubricants, or the like to inanimate objects. Such liquids are often applied by wetting an applicator with a liquid and then contacting the surface to be treated with the applicator. It is quite easy to spill materials when pouring liquids onto applicators and it is often inconvenient to carry bottles or cans of the liquid about if it is to be applied on a regular basis.

Liquids are often carried about in small bottles or tubes and, more recently, small flexible packets of liquids have been commercially available. These containers still require additional applicator means.

U.S. Pat. No. 3,334,374 describes an applicator pad which contains relatively small amounts of liquid in microcapsules of less than 1,000 microns. The pad comprises a thin flat flexible compressible sealed pouch with the microcapsules therein. At least one wall of the pouch includes a conformable liquid-permeable fibrous web. Rubbing the pouch with pressure against a surface will rupture the enclosed microcapsules and transfer the encapsulated liquid through the fibrous web. Because the entire pad can be accidentally subjected to pressure, normal handling can prematurely rupture capsules and cause the liquid to transfer to inappropriate surfaces.

SUMMARY OF THE INVENTION

A dry liquid applicator has a support surface, at least a portion of said support surface having a coating or layer of relatively large microcapsules containing a liquid. A liquid permeable material overlays the microcapsules and a top protective layer creates a protective well around at least a portion of the microcapsules. The permeable material also covers said at least a portion of the microcapsules.

DETAILED DESCRIPTION OF THE DRAWINGS

Figure 1:
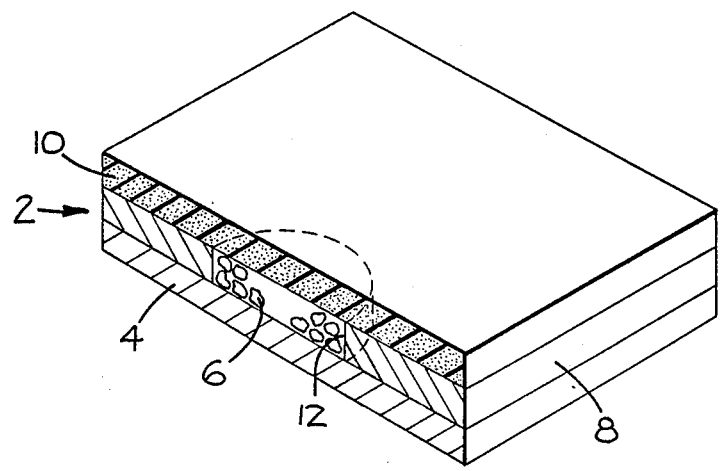
FIG. 1 is a cutaway perspective of a dry liquid applicator with a continuous, liquid permeable cover.

FIG. 1 shows a dry liquid applicator 2 having a support layer 4 and a structural definition layer 8. The structural definition layer 8 is discontinued or cut to provide a wall 12 which prevents facile contact with microcapsules 6 below the top of the definition layer 8. A continuous liquid-permeable, flexible layer 10 is provided over the definition layer 8. Pressure on the flexible layer 10 immediately over the microcapsules 6 will cause some of the microcapsules 6 to rupture and allow the enclosed liquid to permeate through the liquid permeable layer 10.

Figure 2:
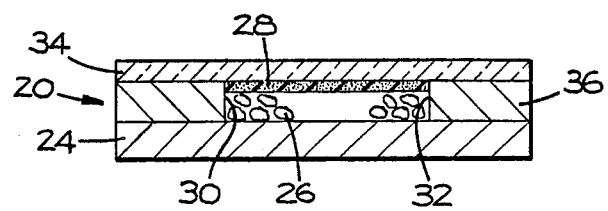
FIG. 2 is a cross section of a dry liquid applicator with a liquid permeable cover co-extensive with liquid-filled microcapsules.

FIG. 2 shows a dry liquid applicator 20 having a support layer 24 and a structural definition layer 36. The structural definition layer is cut or hollowed out to provide an area defined by walls 30 and 32 in said structural definition layer 36. Within this area are microcapsules containing liquid 26 and a flexible liquid-permeable layer 28. An optional protective cover film 34 is also shown. After peeling off the removable protective cover film 34, pressure against the liquid-permeable layer 28 will cause some of the microcapsules 26 to rupture allowing the liquid contained therein to penetrate the liquid permeable layer 28 and be transferred to an external surface.

DETAILED DESCRIPTION OF THE INVENTION

The applicator device of the present invention comprises a minimum of three distinct elements, the support/structural layer, the microcapsules and the liquid permeable layer.

The support/structural layer may be a single layer with a crisply defined depression or partially cut out area therein, or may be constructed with two layers, one continuous and the other with a hole therein. What is essential is that a well or depression or hole is created which does not pass entirely through the support structured layer. It is preferred that the bottom of the well is not readily penetrated by liquid within the capsules. If the liquid will not show through the exterior of the bottom of the well in less than thirty seconds, this is sufficient for liquid barrier properties. It is preferred that it be completely impermeable to the liquid. It is also desirable that the support layer (at least directly under the microcapsules) is less flexible than the liquid permeable layer. This support is desirable for the protection of the microcapsules. It is also usually desirable that the structural portion of the support/structural layer is not readily penetrable by the liquid within the capsules. However, for some applications a degree of liquid transport through the support layer may serve to indicate that the microcapsules have previously been broken. This is especially true where multiple cavities are present on one device. If it were readily liquid penetrable, liquid would pass horizontally rather than through the flexible liquid permeable layer.

The composition of the support/structural layer may be paper, polymeric film, coated paper, polymeric foam, elastomer or the like. Paper, polymer film and coated paper are preferred.

Pressure-rupturable capsules, comprising thin, self-supporting, polymeric shells around quantities of the desired liquid agent, are placed within the device before it is finally sealed. The capsules may be formed with a wide variety of aqueous or organic liquid fills by many processes known to the art, as for example as described in U.S. Pat. No. 2,800,457 or U.S. Pat. No. 2,766,478, or by other known techniques. Tough, useful capsules having good storage and handling characteristics have been found to be those having aminoplast polymer shell walls around finely divided particles of the liquid agent. Such capsules may be made by the procedure described in U.S. Pat. No. 3,516,941 or U.S. Pat. No. 3,423,489 and are preferably urea-aldehyde reaction products, e.g., urea and formaldehyde, glutaraldehyde, etc. Liquid filled closed-cell foams (which can be made by frothing or other techniques) are also useful.

The manufactured capsules are dry, and in small microscopic sizes (microcapsules) may have the appearance of a fine powder; in larger sizes the capsules are visually observable as capsules to the unaided eye. The aminoplast shelled capsules may be stored for long periods of time without deterioration, evaporation or reaction of their liquid contents. Typically, they are impervious to moisture.

Under moderate pressure the capsules burst, discharging their liquid fill. In using the applicators of the present invention, the liquid agent may be freed by such methods as squeezing the pad between the fingers preliminary to application, or pressing the pad against the object to which the liquid is to be applied. As the pad is pressed or rubbed against the object, the released liquid penetrates the porous facing member and soaks into the object or is distributed over its surface.

For good results the capsules should have an average diameter in the range of 200–3000 microns. Capsules more than 3000 microns in diameter are less desired because to make them handleable in manufacturing and processing they must have rather thick, strong shells that hinder their easy rupture in an applicator pad. At sizes smaller than 200 microns, the capsules become rather difficult to rupture by hand pressure. Further, with small capsules the shells comprise too large a proportion, and the usable liquid too small a proportion, of the applicator contents Since the capsule shell may act as an absorbent, small capsules with their accompanying large surface area of shell upon rupture may also be disadvantageous by causing too great an adsorption of liquid released from the capsules. Preferably the capsules are in a range of about 300–1000 microns in diameter.

The liquid fill normally comprises about 50 to 99 weight percent of the capsules. Capsules are included in an amount principally determined by the amount of liquid that is normally needed or desirable in a single application of the applicator. The amount of capsules should be such as not to become such a thick layer that the applicator becomes unwieldly.

Large microcapsules preferably can be made of encapsulated liquids such as oil compositions added to carrying media such as cosmetic or medical compositions. The encapsulated materials in the form of polymeric microcapsules having average microcapsule diameters between 200 and 3000 microns can contain media such as skin creams, liquid soaps, cleansing gels, cleansing creams, cleansing lotions, lotions, styptics, insect repellants, UV absorbers (i.e., sun screens) anti-infamatants, bacteriacides, fungicides, astringents, and the like.

General types of ingredients in the cosmetic and medicinal compositions in the microcapsules are surfactants, oils, pigments, stabilizers, aromatic oils, water, carboxylic acids, olefin glycols, gelatin, moisturizers, waxes, fragrances, lanolin, and the like.

In a preferred practice of the present invention, microcapsules are prepared by polymerization such as in situ aminoplast polymerization. The techniques disclosed, generally referred to as an in situ polymerization reaction, yield, for example, an aminoplast resin capsule wall material. In the process, an oil phase with a polymeric material dissolved therein is dispersed in an aqueous phase containing the aminoplast resin precursors by applying shear agitation. Addition of an acid catalyst initiates the polycondensation of the aminoplast precursors, resulting in the deposition of the aminoplast resin about the dispersed droplets of the oil phase, producing the microcapsules.

Typical cosmetic emollient oils are organic liquids with viscosities between 2 and 150 cp at 20° C., preferably between 2 and 100 cp. the oils preferably have molecular weights in excess of 100, more preferably in excess of 125 and most preferably between 125 and 500. Examples of commercial oils used as cosmetic emollient oils include mineral oil, castor oil, vegetable oil, corn oil, peanut oil, jojoba oil, 2-ethylhexyl oxystearate (and other alkyl oxystearates), acetulated lanolin alcohol, alkyl palmitates such as isopropyl palmitate, 2-ethylhexyl palmitate, glyceral triacetates, disopropyl adipate, dioctyl adipate (and other alkyl adipates), isopropyl myristate, $C_{12}$ to $C_{15}$ alcohol benzoates, and the like.

The polymeric additive should be dispersible or soluble in the oil so as to increase its viscosity. These materials are preferably polymers although waxy substances may be used with less desirable results. The polymers should be oleophilic to be swollen by or soluble in the oil. Examples of preferred polymers include polyolefins, polystyrene, polybutadiene, graft or block polymers of these materials such as a polystyrene-polybutadienepolystyrene block copolymer, polyacrylates, natural rubber (not heavily vulcanized), polyisoprene, polyisobutylene, cellulose acetate esters such as cellulose acetate butyrate and cellulose acetate proprionate, and the like.

The preferred process of the present invention for making large microcapsules utilizes the addition of viscosity increasing materials selected from the group consisting of particulates (e.g., clays and polymeric particles), waxes, and polymeric additives to cosmetic emollient oils to increase their viscosity and then using the higher viscosity oil mixtures or solutions in a microencapsulation process to produce particles of a larger size than would ordinarily be formed in encapsulation of the oil without additives under identical encapsulation reaction conditions. Polymeric additives are especially preferred because they are more consistent and repeatable in their performance and because they hold the oil better on the skin. These oils with increased viscosity are particularly beneficial in encapsulation processes where shear forces are used to maintain a dispersed phase of oil in the reaction vessel. The weight percentage of polymer
in the media is generally between ½ and 35%, preferably between 5 and 30% by weight of polymer to weight of oil.

The shell material of the capsules may be any of the various materials known to be useful in forming capsules such as organic polymers, particularly phenolicaldehydes, urea-aldehydes, acrylic polymers, addition polymers, condensation polymers, natural resins such as gelatin and agar-agar, and any of the other many well-known capsule making materials. The capsules are preferably between 200 and 3000 microns in diameter, more preferably between 300 and 1500 microns and most preferably between 600 and 1000 microns. Preferably they have a loading of (emollient and polymer)/(shell) at least 2:1 and preferably between 3:1 and 10:1. It is particularly advantageous to use shell materials which when broken to release their load provide a tactile indication that sufficient pressure has been applied. Brittle polymeric materials are therefore especially preferred, and the phenolic-aldehyde and urea aldehydes are most preferred in that class. For larger or water-filled capsules, wax or thermoplastic shells are particularly useful.

Additional additives such as perfumes, pigments, vitamins, sunscreens, insect repellants and medication may be added to the oil/polymer mixture.

EXAMPLE 1

Urea formaldehyde capsules of the type described in U.S. Pat. No. 3,516,941 were prepared using a fragrance oil thickened with 2.5% by weight Kraton 1107 as the fill. The capsules thus formed were wet-filtered through a #18 standard sieve (1000 micron opening) onto a #30 sieve (595 micron opening). The fraction retained on the #30 sieve was dewatered in a Buchner funnel and tray dried at 120° F. (49° C.) for 24 hours.

A liquid sampling device was fabricated by screen printing a water-borne adhesive onto a 8 pt. base paper sheet, laminating a 28 pt. paper spacer with one inch (2.5 cm) diameter hole to the base, and sprinkling the dry capsules onto the wet adhesive which was exposed within the opening. A brush was used to seat the capsules in the adhesive, to increase the percentage of the area covered by capsules, and to remove excess capsules from the cavity. A second silk screen application of water-borne adhesive was used to laminate a non-woven polyester fiber web (0.75 oz./square yd., 17.6 g/m$^2$) to the top of the spacer. An 8 pt. paper cover (bearing printed graphics and a UV cured gloss coating) was then glued to the non-woven fabric so that the one inch diameter hole in the decorative cover was aligned with the corresponding hole in the spacer. A second printed UV gloss coated piece of 8 pt. paper was then adhered to the base of the sampler and folded to provide a flap covering the exposed portion of the non-woven fabric thus protecting the capsules from premature rupture during handling. Further protection against rupture or undesirable release of liquid from the sampler following capsule rupture was provided by the addition of an optional polyester film layer held over the opening by a repositionable adhesive allowing the sampler to be opened, used, and resealed.

EXAMPLE 2

A liquid sampler was prepared using the capsules of Example 1. The 8 pt. base paper was laminated by means of Scotch TM #415 double coated film tape to a 20 pt. paper spacer with a one inch diameter hole. Capsules were sprinkled onto the exposed pressure sensitive adhesive and the excess removed from the opening with a brush as before. Additional capsules were positioned on a heat fusible non-woven fabric manufactured by Stacy Industries, Inc., Wood-ridge, N.J. by means of a mask and fused to the web by mild heating. After excess capsules were removed, the nonwoven fabric was aligned with the capsules positioned over the well in the base/spacer and adhered to the spacer by heating A decorative cover similar to that of Example 1 was bonded over the non-woven by means of double coated film tape.

EXAMPLE 3

A liquid sampler was prepared in the manner of Example 1 except that two 20 pt. paper spacers bonded together with water-borne adhesive were substituted for the single 28 pt. spacer to provide a construction with a deeper well which was more resistant to accidental capsule rupture.

Many variations in the structure of the liquid applicator devices of the present invention are possible. All of the structures have certain features in common.

There is a support layer and on one side of said support layer are liquid containing microcapsules. A means for providing protective walls or a raised area around the microcapsules are present preferably at least to the height of said microcapsules and more preferably above the highest level of said microcapsules. A flexible, liquid-permeable material overlays the microcapsules. Beyond these minimum structural requirements, many variations in the structure of the sheet may be practiced. Among those variations are:

1. Flat support layer, flat structural layer with a hole defining a well, microcapsules in the well and a flexible, liquid permeable layer either: (a) co-extensive with the well hole, (b) extending over the well hole onto the structural surface, or (c) extending over the microcapsules and between the structural layer and support layer.

2. Thick, flat support layer with embossed or cut depression holding microcapsules and a flexible, liquid permeable layer either co-extensive with the depression (hole) or extending over the depression onto at least a portion of the top support layer surface.

3. An embossed or cut support layer with a structural layer having a hole therein which at least in part overlaps the embossment or hole with microcapsules therein.

EXAMPLE 4

A liquid sampler was prepared in the manner of Example 2 except that 2.5 mm capsules of the type described in U.S. Pat. No. 3,423,489 using a solution of propylene glycol in water as the fill and wax as the shell wall were used with a 5 mm spacer.

EXAMPLE 5

A liquid sampler was prepared using capsules of Example 4 which had been close packed in a monolayer on the substrate and warmed until the walls merged to form a closed, multicelled, liquid filled wax structure. A 5 mm spacer and porous non-woven cover were then applied as in Example 4.

The flexible, liquid-permeable layer may be between the support and structural layer or over the structural layer.

Any number of variants such as two layer structural support layers (with the flexible, liquid permeable layer between the layers), transparent cover films, flaps extending over the depressions or wells, pressure sensitive adhesives holding flaps and cover sheets over the depressions or wells of microcapsules, and the like, may be used in combination with the above structures.

We claim:

1. An applicator device capable of carrying liquid material to be applied to a surface comprising a flat support layer, liquid containing microcapsules of between 200 and 300 microns on at least one surface of said support layer, a flat structural layer with a hole therein for providing a raised area around all of said microcapsules, and a flexible, liquid-permeable material overlaying the microcapsules, said support layer being less flexible than said liquid permeable material, and said microcapsules being bonded to said support layer by an adhesive, said raised area being above the highest level of said microcapsules.

2. The device of claim 1 wherein said raised area comprises a separate sheet of material with a hole therein that defines walls around said microcapsules.

3. The device of claim 2 wherein said microcapsules have an average diameter between 200 and 1000 microns.

4. The device of claim 2 wherein a cover sheet is removably placed over said liquid-permeable material.

5. The device of claim 1 wherein said raised area is formed by folds, embossment, or shaping of said support means.

6. The device of claim 5 wherein said microcapsules have an average diameter between 200 and 1000 microns.

7. The device of claim 5 wherein a cover sheet is removably placed over said liquid-permeable material.

8. The device of claim 6 wherein a cover sheet is removably placed over said liquid-permeable material.

9. The device of claim 1 wherein said microcapsules have an average diameter between 200 and 1000 microns.

10. The device of claim 9 wherein a cover sheet is removably placed over said liquid-permeable material.

11. The device of claim 1 wherein a cover sheet is removably placed over said liquid-permeable material.

* * * * *

UNITED STATES PATENT AND TRADEMARK OFFICE
CERTIFICATE OF CORRECTION

PATENT NO. : 4,878,775
DATED : November 7, 1989
INVENTOR(S) : Norbury and Pendergrass It is certified that error appears in the above-identified patent and that said Letters Patent is hereby corrected as shown below:

Column 4, line 45, insert --to oil-- after "polymer".

Claim 1, column 6, line 57, "300" should be --3000--.

Signed and Sealed this

Fourteenth Day of May, 1991

Attest:

HARRY F. MANBECK, JR.

Attesting Officer

Commissioner of Patents and Trademarks